United States Patent
Harper et al.

(10) Patent No.: US 12,024,689 B2
(45) Date of Patent: Jul. 2, 2024

(54) FOAMABLE SOLID CLEANSER

(71) Applicant: Johnson & Johnson Consumer Inc., Skillman, NJ (US)

(72) Inventors: Donald L. Harper, Flemington, NJ (US); Hima Sadavrati, Bridgewater, NJ (US); Shailendra Singh, Monroe Township, NJ (US); Thomas Joseph, Oakford, PA (US); Marcee Martinez, Cedar Knolls, NJ (US); Anthony Geonnotti, III, Princeton, NJ (US); Aliaksandr Zhuk, Warrington, PA (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 927 days.

(21) Appl. No.: 16/668,663

(22) Filed: Oct. 30, 2019

(65) Prior Publication Data

US 2020/0140781 A1    May 7, 2020

Related U.S. Application Data

(60) Provisional application No. 62/754,885, filed on Nov. 2, 2018.

(51) Int. Cl.
    *C11D 1/00*    (2006.01)
    *A61K 8/19*    (2006.01)
    (Continued)

(52) U.S. Cl.
    CPC .............. *C11D 1/123* (2013.01); *C11D 1/37* (2013.01); *C11D 3/122* (2013.01); *C11D 17/0073* (2013.01)

(58) Field of Classification Search
    CPC .... C11D 1/00; C11D 1/12; C11D 1/37; C11D 3/042; C11D 3/044; C11D 3/10;
    (Continued)

(56) References Cited

U.S. PATENT DOCUMENTS

| | | | | |
|---|---|---|---|---|
| 6,313,086 | B1 * | 11/2001 | Askew | C11D 17/065 510/345 |
| 6,506,713 | B1 * | 1/2003 | Slavtcheff | A61K 8/365 424/404 |

(Continued)

FOREIGN PATENT DOCUMENTS

| | | |
|---|---|---|
| CN | 1311664 A | 9/2001 |
| DE | 19745964 A1 | 6/1998 |

(Continued)

OTHER PUBLICATIONS

Database GNPD [Online] MINTEL; May 22, 2017 (May 22, 2017), anonymous: "Foaming Bath Salts", 2 pages—XP055649932, retrived from www.gnpd.com Database acession No. 4831081.abstract.*

(Continued)

*Primary Examiner* — Brian P Mruk
(74) *Attorney, Agent, or Firm* — Rachel Chaves (57) ABSTRACT

A solid cleansing product including at least a first surfactant and a second surfactant present in a combined surfactant weight amount; at least a first buffering agent and a second buffering agent a present in a combined buffering agent weight amount; and magnesium sulfate; where the combined buffering agent weight amount is greater than the combined surfactant weight amount.

16 Claims, 7 Drawing Sheets

(51) Int. Cl.
*A61K 8/23* (2006.01)
*A61Q 19/10* (2006.01)
*C11D 1/12* (2006.01)
*C11D 1/37* (2006.01)
*C11D 3/10* (2006.01)
*C11D 3/12* (2006.01)
*C11D 17/00* (2006.01)

(58) Field of Classification Search
CPC ..... C11D 3/12; C11D 3/2086; C11D 17/0065; A61K 8/0216; A61K 8/022; A61K 8/19; A61K 8/23; A61K 8/361; A61K 2800/596; A61Q 19/10
See application file for complete search history.

(56) References Cited

U.S. PATENT DOCUMENTS

2003/0059387 A1 3/2003 Bergquist
2006/0079433 A1 4/2006 Hecht

FOREIGN PATENT DOCUMENTS

| | | | |
|---|---|---|---|
| EP | 693549 A1 | 1/1996 | |
| RU | 2251405 C2 | 5/2005 | |
| RU | 2350313 C2 | 3/2009 | |
| RU | 2016139405 A3 | 7/2018 | |
| WO | WO 99/19430 * | 4/1999 | ............ C11D 1/37 |
| WO | WO00/07561 A1 | 2/2000 | |
| WO | WO00/07564 A1 | 2/2000 | |

OTHER PUBLICATIONS

Database GNPD [online] MINTEL; Mar. 29, 2018, anonymous: "Unicorn Fizzy Donut", XP055649942, retrieved from www.gnpd.com Database accession No. 5553819.

Database GNPD [online] MINTEL; Mar. 16, 2017, anonymous: "Tingles Lemonade Bath Fizz", XP055650871, retrieved from www.gnpd.com Database accession No. 4679897.

Database GNPD [online] MINTEL; Sep. 18, 2009, anonymous: "Skin Softening Bath Salts", XP055649822, retrieved from www.gnpd.com Database accession No. 1176860.

PCT Written Opinion for corresponding Intl Appln. No. PCT/IB2019/059316.

* cited by examiner

FOAMABLE SOLID CLEANSER

CROSS-REFERENCE TO RELATED APPLICATIONS

This application claims priority to U.S. Patent Application No. 62/754,885, filed Nov. 2, 2018, the entire contents of which are incorporated by reference herein.

FIELD

The present invention relates to cleansing products, and in particular solid cleansing products. The solid cleansing products are foamable in the presence of a fluid, such as water, and in some aspects may be in the form of a loose powder, a capsule, or a pressed tablet.

BACKGROUND

Cleansing products come in various forms, including liquid forms. Liquid cleansing forms are quite useful and effective, but they are susceptible to leaks and spills, and also typically require larger packages, such as bottles. For this reason, a solid cleansing product may be desired. Solid cleansing products are dissolvable in the presence of a fluid. Solid cleansers, however, do not often foam to a desired profile or volume, that is, they do not foam quickly enough, nor do they have the desired foam stability.

"Bath Bombs" are products that are generally solid in nature and dissolve in the presence of water, where the bath bomb includes a cleansing product contained therein. Bath Bombs are generally hard-packed mixtures of dry ingredients that effervesce when wetted. These products generally react vigorously in the presence of water to provide a fizzing and complete dissolution within less than 5 minutes. Bath bombs are known to provide one or more elements to bath water, such as fragrance, oils, bubbles or colors. However, bath bombs typically do not provide a desired foaming profile or volume when used, nor do bath bombs provide any moisturizing effect or other skin benefits, in particular, facial benefits, such as acne treatment. Bath bombs are typically used to provide elements to a large body of water (such as a full bathtub), but not to provide foamed cleansing to a user. Bath bombs are typically not suitable for dissolution in the hands of a user and subsequently used on the skin or face of the user.

There is a need for a solid cleansing product, particularly one made from powdered materials, which provides a combination of foaming, cleansing, moisturizing and skin conditioning ingredients. The present invention provides a solid cleansing product, which has a desirable volume of foam generated and desirable foam stability, as well as providing desired cleansing levels. The solid cleansing products may be in the form of concentrated cleansing tablets, which transform into a bubbly, cushiony foam at a rapid pace to give a desired level of cleansing without harshness, dryness or irritation to the user's skin. Certain embodiments of the solid cleansing product may also include moisturizing agents to leave user's skin feeling moisturized.

DETAILED DESCRIPTION

As used herein, the term "solid" refers to a material that is not in liquid form. Solid products may include flowable granules or powders, or may include a larger solid form, such as a tablet or pressed tablet. Desirably, solid products as described herein are anhydrous in nature. It is desired that the cleansing products herein be substantially free of added water, and is more desired that the cleansing products herein be free of added water. The cleansing products may include trace levels of water due to the presence water in ingredients such as fragrances, extracts, and the like, as well as due to the presence of of moisture in the air, however, the amount of trace water in the cleansing products should be less than 0.2% by weight of the formulation, more desirably less than 0.1% by weight of the formulation, and more desirably less than 0.01% by weight of the formulation.

The cleansing product described herein may be in one of a number of different forms. It may be in the form of a pressed tablet, as will be described in greater detail below. The cleansing product may be a powdered material in a sachet, capsule, or other storage unit. The cleansing product may be encapsulated in an outer capsule or other shell, may be encapsulated within an outer dissolvable film or casing, where the outer material may be either separated or broken to release the cleansing product, or dissolved during use, thereby releasing the cleansing components contained therein. In some aspects, the cleansing product is a granulated or powdered material, which may be dispensed from a storage container prior to use.

It is most desired that the components of the cleansing product be solid, such as in the form of a powder or granules. Most desirably, the components are in the form of powders or granules, and if desired, the components may be subjected to a milling or rolling step prior to the formation of the cleansing product. As used herein, the term "powder" refers to a particulate material having an average cross-sectional diameter of less than about 2.1 microns, or less than about 1.1 microns, or less than about 0.8 microns. It is noted that the term "diameter" does not necessarily require that the particle be spherical in shape, and can refer to particles having any cross-sectional configuration.

The cleansing product includes a number of components, including at least one surfactant. Desirably, the cleansing product includes at least two surfactants, where the first and second surfactants differ from each other. The cleansing product may also include at least one skin conditioning agent, such as shea butter (or alternatively shea butter powder including a blend of shea butter in a silica carrier, sold as Jarplex SB60 by Jarchem Industries Inc.). The cleansing product may also include a buffering agent. The cleansing product also includes a binder, and may optionally include a bulking agent. In desired embodiments, the cleansing product includes a glidant, such as silica, which aids in processing. The cleansing product may also include an anticaking agent. Optionally, the cleansing product may include a skin benefit agent such as an anti-acne agent, anti-aging agents, antimicrobial agents, and the like.

Cleansing products may also include other additives such as colors or fragrances, if desired.

As noted above, cleansing product includes at least one surfactant, and desirably includes more than one surfactant, where the first and second surfactants are different from each other. In some aspects, the surfactants are each independently sulfate-containing surfactants. Surfactants useful in the present invention include anionic such as alcohol ether sulfates, linear alkylbenzene sulfonates, sodium cocoyl isethionate, sodium coco-sulfate, and acyl isethionates. Preferably, the first surfactant is sodium cocoyl isethionate and second surfactant is sodium coco-sulfate. Other surfactants useful in the present invention include cationic surfactants, such as quaternary ammonium salts, amine oxides, and ester quats; amphoteric surfactants, such as betaines, amidobetaines, ester betaines, and amphoacetates; and nonionic surfactants, such as alky polyglycosides, alcohol ethoxylates, and fatty alkanol amides. In embodiments where there is more than one surfactant, the first surfactant and second surfactant may both be the anionic, nonionic, cationic, or amphoteric, or the first and second surfactants may be different in ionic nature.

Surfactants may be present in any amount from about 1% to about 50% by weight of the overall product, or may be present in an amount from about 5% to about 40% by weight of the overall product, or may be present in an amount of from about 10% to about 30% by weight of the overall product. If more than one surfactant is used, each surfactant may be present in the same weight amount or may be present in different weight amounts. The first surfactant and second surfactant may be present in weight ratios of from 1:1 to 10:1, or from 1:1 to 5:1, or from 1:1 to 3:1, or from 1:1 to about 1:1.5, respectively. Preferably, the first surfactant and second surfactant may be present in weight ratios of about 1:1.

Binding agents useful in the present invention include, but not limited to lactose, methyl cellulose, hydroxypropyl cellulose, hydroxypropylmethyl cellulose, gelatin, gum arabic, ethyl cellulose, polyvinyl alcohol, pullulan, pregelatinized starch, agar, tragacanth, sodium alginate, propyleneglycol alginate, and the like. One such binding agent is lactose monohydrate, while other binding agents include microcrystalline cellulose, and pregelatinized starch. One such microcrystalline cellulose that may be used in the invention includes a silicified microcrystalline cellulose sold under the name ProSolv SMCC (sold by JRS Pharma). ProSolv SMCC is a combination of microcrystalline cellulose and colloidal silicon dioxide, and may be available with an average particle size of from 50 to 65 micrometers (ProSolv SMCC 50 and ProSolv SMCC 50 LD) and an average particle size of 125 micrometers (ProSolv SMCC 90 and ProSolv SMCC 90 HD). The binding agent may be present in any desired amount, including from about 10% to about 40% by weight of the cleansing product. In some aspects the binding agent is present in an amount of from about 20% to about 30% by weight of the cleansing product. In some aspects the binding agent may be present in an amount that is less than the combined weight of all surfactants.

Skin conditioning agent useful in the present invention include aloe extracts, allantoin, bisabolol, ceramides, dimethicone, hyaluronic acid, biosaccharide gum-1, ethylhexylglycerin, pentylene glycol, hydrogenated polydecene, octyldodecyl oleate, dipotassium glycyrrhizate and potassium cetyl phosphate. Emulsifiers may be present in an amount of about 1% to about 10% by weight of the cleansing product, or from about 4% to about 6% by weight of the cleansing product.

Bulking agents may optionally be used in the cleansing products of the present invention. Suitable bulking agents include, for example, corn starch, such as zea may corn starch (sold by Ingredion). When used, bulking agents may be present in an amount of about 3% to about 10% by weight of the cleansing product, or from about 5% to about 8% by weight of the cleansing product.

The present invention also includes a buffering agent. In desired embodiment, the present invention includes two distinctly different buffering agents. The first buffering agent is basic in nature, while the second buffering agent is acidic in nature. One example of a suitable first buffering agent includes sodium bicarbonate, and an example of a suitable second buffering agent includes citric acid. Buffering agents may be used in combined weights of from about 10% to about 50% by weight of the cleansing product, or from about 16% to about 48% by weight of the cleansing product, or from about 34% to about 48% by weight of the cleansing product. It is most desirable that more than one different buffering agent be used, where the first buffering agent is present in an amount that is substantially the same weight amount as the second buffering agent. In some aspects, the first buffering agent may be present in an amount of from about 5% to about 25% by weight of the cleansing product, and the second buffering agent may be present in an amount of from about 5% to about 25% by weight of the cleansing product. As used herein, the term "substantially the same weight amount" means that the first buffering agent and the second buffering agent do not differ in weight amount from each other by more than about 5%. The first buffering agent and second buffering agent may be present in weight ratios of from 1:1 to 10:1, or from 1:1 to 5:1, or from 1:1 to 3:1, respectively. Preferably, the buffering agent and second buffering agent may be present in weight ratios of 1:1.

The total weight amount of all surfactants and all buffering agents may be from about 50% to about 80% of the total weight of the cleansing product. In some aspects, the total weight amount of the surfactants and buffering agents in the cleansing product may be from about 54-70% by weight of the total cleansing product.

In embodiments where the cleansing product is in the form of a pressed tablet, it is desired to include a glidant, which improves the flowability of the powders and aids in the processing of the tablet. Glidants promote the flow of granules or powders by reducing the friction between powders. Glidants may be present in an amount of from about 0.1% to about 2% by weight of the cleansing product, or from about 0.5% to about 1% by weight of the cleansing product. Examples of glidants include, for example, magnesium stearate, fumed silica, starch and talc. The pressed cleansing tablet may additionally include a lubricant, such as magnesium stearate, which prevents adhesion of the tablet.

The cleansing product may include an anticaking agent, which is an additive in cleansing powder to prevent the formation of agglomerated materials and to improve flow during formation of the final product, as well as for easing packaging, transport, and consumption. Some anticaking agents are soluble in water, while others are soluble in alcohols or other organic solvents. They function either by absorbing excess moisture or by coating particles and thereby making them repel water more effectively. Suitable anticaking agents include, for example, magnesium sulfate. When used, the anti-caking agent may be present in an amount of from about 3% to about 12% by weight of the cleansing product, and may be from about 1% to about 20% by weight of the cleansing product.

The cleansing product may include colorants and/or fragrances as desired. When used, colorants may be used in an amount of from about 0.1% to about 2% by weight of the cleansing product. In some aspects, the cleansing product may include multiple colorants, and in some aspects, the cleansing product may be a pressed tablet that has distinct layers of colors or includes a color scheme in which the product includes lines or layers of colors. The cleansing product may include a fragrance, where when used, the fragrance is used in an amount of from about 0.01% to about 0.5% by weight of the cleansing product. The cleansing product may be free of added colorants or added fragrances.

The cleansing product may include one or more additional active agents, such as anti-acne agents, anti-aging agents, antimicrobial agents, and the like. Such skin benefit ingredients/carriers include, for example, one or more of the following ingredients: retinol, retinyl esters, tetronic acid, tetronic acid derivatives, hydroquinone, kojic acid, gallic acid, arbutin, ct-hydroxy acids, niacinamide, pyridoxine, ascorbic acid, vitamin E and derivatives, aloe, salicylic acid, benzoyl peroxide, witch hazel, caffeine, zinc pyrithione, fatty acid esters of ascorbic acid, colloidal oatmeal, acids such as alpha hydroxy acid, polyhydroxy acid, and beta hydroxy acid, enzymes such as chlorella, papaya, and papain, N-acetylglucosamine, and gluconolactone. Other skin care ingredients and carriers are known to those of skill in the art and may be used in the compositions of the invention.

Additional skin benefit ingredients that may be included in the composition of the invention include one or more of the following ingredients: emulsifying agent such as potassium cetyl phosphate, glyceryl stearate and PEG-100 stearate; conditioning agents, such as polyquaterniums, cotton powder and panthenol; pearlizing agents, such as glycol distearate, distearyl ether, and mica; UV filters, such as octocrylene, octyl methoxycinnamate, benzophenone-4, titanium dioxide, and zinc oxide; exfoliation additives, such as apricot seeds, walnut shells, polymeric or cellulose beads, and pumice; silicones such as dimethicone, cyclomethicone, and amodimethicone; moisturizing agents such as petrolatum, sunflower oil, fatty alcohols, glucose, ceramides, hyaluronic acid, lactic acid, gelatin, ascorbic acid, allantoin, milk protein, maltodextrin, zinc gluconate, urea and shea butter; foam stabilizers such as cocamide MEA and cocamide DEA; anti-bacterial agents such as triclosan; humectants such as glycerin; thickening agents such as guar sodium chloride, and carbomer; hair and skin damage repair agents such as proteins, hydrolyzed proteins, and hydrolyzed collagen; foam boosters such as cocamide MIPA; preservatives such as phenoyethanol, ethylhexyl glycerin, sodium benzoate, and formaldehyde donors; and fragrances. If used, the additional skin benefit agent is preferably an emulsifying agent such as potassium cetyl phosphate and it is in an amount from about 1% to about 10%, more preferably from about 2 to about 5%.

It may be desired that the final product include one or more superdisintegrants. For example, the product may include Ac-Di-Sol® Croscarmellose Sodium, which is an internally cross-linked sodium carboxymethyl cellulose (NaCMC) that aids in the disintegration and dissolution of pharmaceutical and dietary supplement tablets, capsules, and granules. If used, a superdisintegrant may be used in an amount of from about 0.01 to about 2% by weight of the final product, or about 0.1 to about 1% by weight of the final product.

As discussed above, the cleansing product may be in any solid form, and in some embodiments, it is desirable that the cleansing product be in the form of a pressed tablet or a loose powder. When a pressed tablet is used, the pressed tablet should have the right balance between compression, friability and dissolution times. The pressed tablet desirably is compressed so that it maintains the shape and feel of a tablet, but allows for a user to break or crush the tablet to reduce the tablet to a powdered or granulated form. The pressed tablet desirably has a friability level that allows it to be crushed by a user, but not so easily friable that it cannot retain its shape when packaged and shipped to users.

The cleansing product is packaged in a substantially water-tight package and desirably is in an air-tight package. For example, the product may be contained within its own single-use packaging, such as a sachet, a capsule, a dissolvable film, a blister package, or other single-wrapped or sealed environment. The user releases the cleansing product from its packaging for use, such as by unwrapping or releasing it from a blister package, or separating/breaking a capsule, or dissolving an outer film. In embodiments where the product is a tablet, it is desired that the user break the tablet apart to form a broken tablet. For example, this may be achieved by crushing the tablet with the user's hands or with a crushing tool, or the tablet may be crushed by twisting the tablet in the user's fingers. In some aspects, the tablet may be crushed through a combination of hand and finger use, such as by placing the tablet within the palm of the user's hand and then using a finger or thumb to crush the tablet within the palm of the user's hand.

In aspects where the cleansing product is in the form of a powder, the user may not need to manipulate the cleansing product to render it more broken apart.

Once crushed or dispensed in the form of a powder, the user may add a small amount of water to the cleansing product (e.g., about 3-10 mL, or about 3-5 mL), and run the wetted cleansing product within the user's hands, fingers, body, face, or hair. By running the wetted product within the user's hands, fingers, body, face or hair, the wetted product forms a foamed cleansing product. The product has the foaming generation rate described below, and desirably within about 2 to about 5 seconds after exposure to water and rubbing within the user's hands, fingers, body, face or hair, at least about 95% of the solid cleansing product becomes a foamed cleansing product. The user then can apply the foamed cleansing product to the area or areas of the user's body as desired, including hands, body, face, or hair, or alternatively, the foamed cleansing product may be formed by directly rubbing the mixture of solid cleansing product and water against the desired body region of the user. When cleansing is complete, the user may rinse the foamed and applied cleansing product with water.

The present invention includes a method of making a solid cleansing product in the form of a pressed tablet. As mentioned above, it is desired that the components of the pressed tablet be in the form of powders, and therefore if desired or if necessary, the method of forming a tablet may include an initial step of rolling or milling individual components into the form of a powder. For example, the first step may be to roll or mill the one or more surfactants into a powder having a particle size of less than about 2 microns in cross-sectional diameter or less than about 1.1 microns in cross-sectional diameter. By way of example, a first surfactant may initially be in the form of flakes and the second surfactant may be in the form of noodles, but each of these surfactants are milled (either together or individually) to form a powder having a desired particle size.

When making a cleansing product described herein, the surfactant (or surfactants, if used) are added to a dry powder blender, such as a LM-40 Blender (manufactured by L.B. Bohle). To the surfactant(s) is added a mixture of other dry components except for the glidant. For example, the mixture of other dry components may include the binding agent(s), bulking agent(s), buffering agent(s), anti-caking agent(s), and other optional components (such as anti-acne agents, colorants, fragrances). These components are then mixed in the Blender for a sufficient time to achieve thorough mixing, which may be about 10 minutes at about 25-50 RPM, or until fully mixed. At the conclusion of this initial mixing stage, the glidant(s) may then be added to the mixture if desired, and the composition with glidant(s) may then be mixed for an additional 5 minutes at about 25-50 RPM, or until fully mixed. Once mixed, the composition is ready for tableting, if the final product is to be made into a tablet.

In embodiments where it is desired that the product be in the form of a tablet, the mixed composition is added to a tableting device, where it is subjected to the force and compression desired to form a suitable tablet which will be suitable for packaging and dispensing, but will also be capable of being used (and crushed, if desired) by a user. The powdered materials may be subjected to a compression force of about 2.0 kN to about 5.0 kN, with an ejection force of about 70 N to about 120 N. The pressed tablet desirably has a weight of about 900 to about 1100 mg, and more desirably about 950 mg to about 1010 mg. The pressed tablet desirably has an average hardness of about 1.0 kp to about 5.0 kp, and more desirably about 1.2 kp to about 3.5 kp. Finally, although the tablet may have any desired thickness, in some aspects it may have a thickness of about 5 mm to about 10 mm, or from about 6 mm to about 8 mm. The final tablet may have any shape desired, including for example a circle, square, hexagon, or other cross-sectional shape, or may be a sphere or cylinder with any desired cross-sectional shape.

The final product, whether in the form of a tablet, or a loose powder, or in any other form, may be packaged in a suitable container. It is desired that the container be substantially air-tight, and more desirably the container is fully air-tight. Once the cleansing product is formed and packaged, it can be distributed to a user or users, and the product may be used by the user as he or she wishes. In addition to providing a cleansing function, the cleansing product may additionally include one or more components to provide other benefits, such as anti-aging or anti-wrinkle benefits.

As discussed above, the present invention provides a foamable cleansing product, which is suitable for use directly on the user's skin, hair or face. It is desirable that the cleansing product generates a suitable Foam Volume, a suitable level of foam stability, and the foam should have a soft, cushiony feel, which may be measured by the bubble size or bubble size distribution after a foam is produced. As used herein, "Foam Volume" refers to the volume of foam generated when the cleansing product is exposed to added water and agitated by the user or by an instrumental method. "Peak Foam Volume" refers to the maximum volume of foam generated during a predetermined agitation time, and soon thereafter the foam begins to decay and lessen. Further, as used herein, "Foam Decay" refers to the percent loss in Foam Volume relative to the Foam Volume at the end of agitation for a predetermined length of time. In use by a consumer, the end of agitation is defined as the point where the product has been combined with water and manipulated by the user (e.g., through rubbing in hands or on skin) to a sufficient point where the foam is generated to a sufficient level. This may be after about 10 seconds of agitation, about 15 seconds of agitation, about 20 seconds of agitation or about 30 seconds of agitation by a user. For the SITA foam test, defined below, agitation is from the propeller pulsed 13 fifteen-second intervals, so that the total agitation time is 195 seconds. Therefore, for the SITA foam test, the "end of agitation" is after this 195 second agitation period. Foam generation time, Foam Volume, Peak Foam Volume, and Foam Decay are based upon the instrumental foam test method described below and, less quantitatively, to the aesthetic evaluations described below.

For the Examples described below, initial screening of the tested formulations involved aesthetic evaluations during intended usage of the product. The product desirably has a foam generation time of about 2-5 seconds, which means that the product begins foaming within about 2 to about 5 seconds after exposure to water and agitation once it is in the form of a powder or crushed product, whether the product is dispensed as a powder or dispensed as a tablet that is crushed by the user. Agitation may include the user rubbing the product (e.g., in the user's hands, on the user's face, or on the user's body). Foam generation time refers to the time required for at least about 95% of the product to react with the water and form a foam. For testing purposes, the Peak Foam Volume and Foam Decay were evaluated quantitatively through the instrumental foam test method described below.

The instrumental foam test method used to quantitatively compare Example formulations was the "SITA Foam Test" which was performed as follows: foam was generated and measured through the use of a SITA Foam Tester R-2000 (sold by SITA Messtechnik GmbH). The SITA Foam Test protocol consists of two phases, both of which are temperature controlled at 30±2 degrees C. The first phase involves "Foam Generation" during which 0.25 gram of test product in 250 mL of moderately hard water (100 ppm $CaCl_2$)) are subjected to thirteen 15-second propeller pulses at 1200 RPM with Foam Volume measurements taken after each pulse (measurements take 10 or less seconds). After the foam from the thirteenth pulse is measured, the "Foam Decay" phase begins for assessing foam stability. "Foam Decay" involves Foam Volume measurements every 60 seconds for 15 minutes. Good foaming products generate at least 500 mL of foam during the "Foam Generation" phase and stable foams decay less than 10% in volume during the 10-minute "Foam Decay" phase. The SITA Foam Test measures incremental Foam Volume during the Foam Generation phase, measures the Peak Foam Volume, and measures incremental Foam Volume during Foam Decay phase.

As used herein, the term "Foam Decay" refers to the amount of reduction in Foam Volume which takes place from the time that the Foam Generation phase ends to 10 minutes later. For example, if a product has a Foam Volume at the end of the Foam Generation phase of 500 mL, and is reduced to 450 mL after 10 minutes, its Foam Decay was 10%. It is desirable that the formulation herein have a Foam Decay value of 10% or less, or of 8% or less, or of 5% or less.

The cleansing products herein may be packaged in any desired method of packaging, which may be dependent upon the particular form of the cleansing product. For example, a pressed tablet may be packaged in a container including a plurality of pressed tablets. Alternatively, a pressed tablet may be packaged in a blister package, whereby the user can dispense one pressed tablet at a time and the remaining tablets may be securely stored in a water-tight or an air-tight blister package. If the cleansing product is in the form of a flowable powder, the cleansing product may be stored in a single-use, air-tight package or sachet, or may be stored in a container (such as a tube, canister, bottle, or ampoule) whereby a desired amount of cleansing product can be dispensed by the user as needed. Put another way, the product may be stored in a multi-use container, where the user takes a desired amount of product for use, or the product may be stored in single-use containers, whereby the package dispenses a single amount of cleansing product upon opening the container.

EXAMPLES

Through the below non-limiting examples, the present invention may be more fully understood. In the below examples, the product was formed (as a powder) and was subject to evaluation within a laboratory setting. After formation of the product, the product was tested informally for aesthetics, such as foaming, skin feel, time to foam, dissolving profile of the components, and dryness after use. In addition, for some of the examples below, attempts were made to form a tablet as described above. If the product did not pass the initial evaluation, either through aesthetic look and feel or through failed tablet making, it was considered to fail and was not tested for additional foam properties. If the product passed the initial evaluation, including either aesthetic test and/or tablet making test, it was subjected to the SITA Foam Test, described herein.

The amount of each component listed in the tables in the below Examples is a weight percent of that component in the final formulation.

Figure 1:
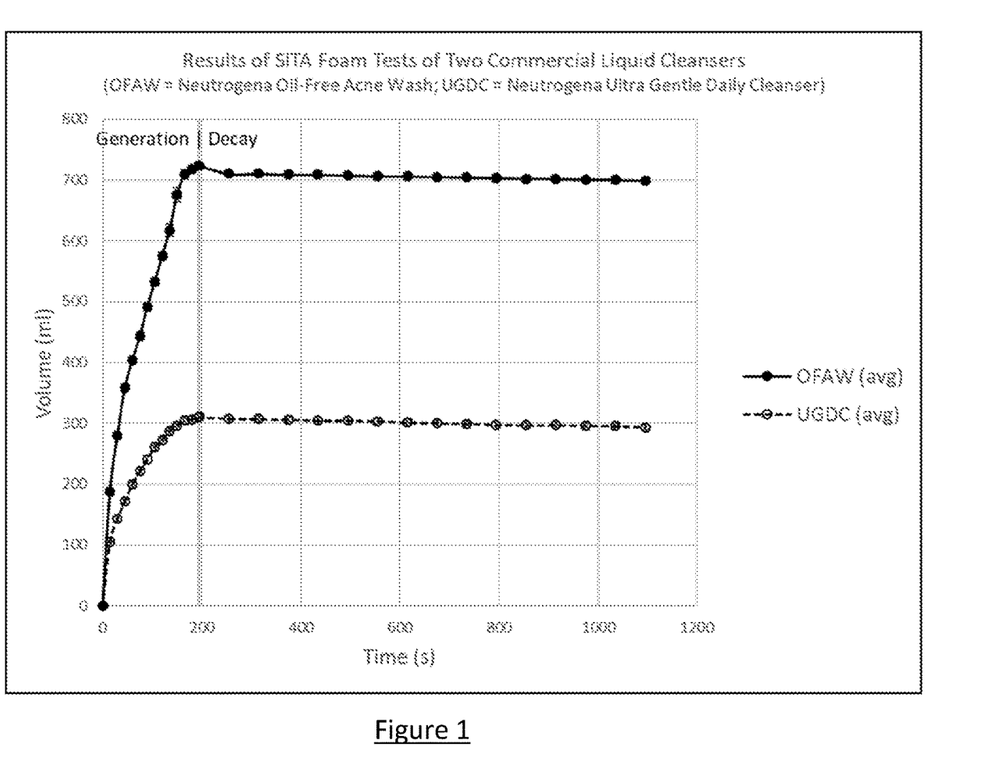
FIG. 1 is a graph depicting the results of foam tests for two commercial liquid cleansers.

Foaming profiles for two commercial liquid cleansing products were evaluated to give comparative levels of foam, and are shown in FIG. 1. One commercial liquid cleanser (NEUTROGENA™ Oil-Free Acne Wash) was found to generate greater than 700 mL of Peak Foam Volume, while a second commercial liquid cleanser (NEUTROGENA™ Ultra Gentle Daily Cleaner) provided about 300 mL of Peak Foam Volume. It is desired that the solid cleansing products described herein have a Peak Foam Volume of about 500 mL or greater.

Based upon the Examples described herein, the presence of magnesium sulfate was found to increase the foaming profile of solid cleansers, however, even in formulations including magnesium sulfate, if the level of one or more of the buffering agents was too high, the foaming profile was found to suffer. Therefore, the present invention includes proper ratios and amounts of components so as to provide suitable and effective foaming profile results.

Example 1A and Examples 2A-D

Example 1A and Examples 2A-2D were prepared to include 40% overall surfactant amount (by weight of the tablet) and a weight ratio of first surfactant to second surfactant of 1:3. The formulations are set forth in the Tables below:

| | | Example | | | | |
|---|---|---|---|---|---|---|
| Component | Function | 1A | 2A | 2B | 2C | 2D |
| Sodium Cocoyl isethionate | First Surfactant | 10.0% | 10.0% | 10.0% | 10.0% | 10.0% |
| Sodium Coco-Sulfate | Second Surfactant | 30.0% | 30.0% | 30.0% | 30.0% | 30.0% |
| Zea May (Corn) Starch | Extender & Conditioning | 0.0% | 0.0% | 4.0% | 4.0% | 4.0% |
| Potassium Cetyl Phosphate | Emulsifying Agent | 4.0% | 0.0% | 0.0% | 0.0% | 0.0% |
| Sodium Bicarbonate | First Buffering Agent | 8.0% | 8.0% | 8.0% | 16.0% | 12.0% |
| Citric Acid | Second Buffering Agent | 8.0% | 8.0% | 8.0% | 8.0% | 12.0% |
| Lactose Monohydrate | Binding Agent | 39.0% | 43.0% | 39.0% | 31.0% | 31.0% |
| Magnesium Stearate | Lubricant | 1.0% | 1.0% | 1.0% | 1.0% | 1.0% |

Figure 3:
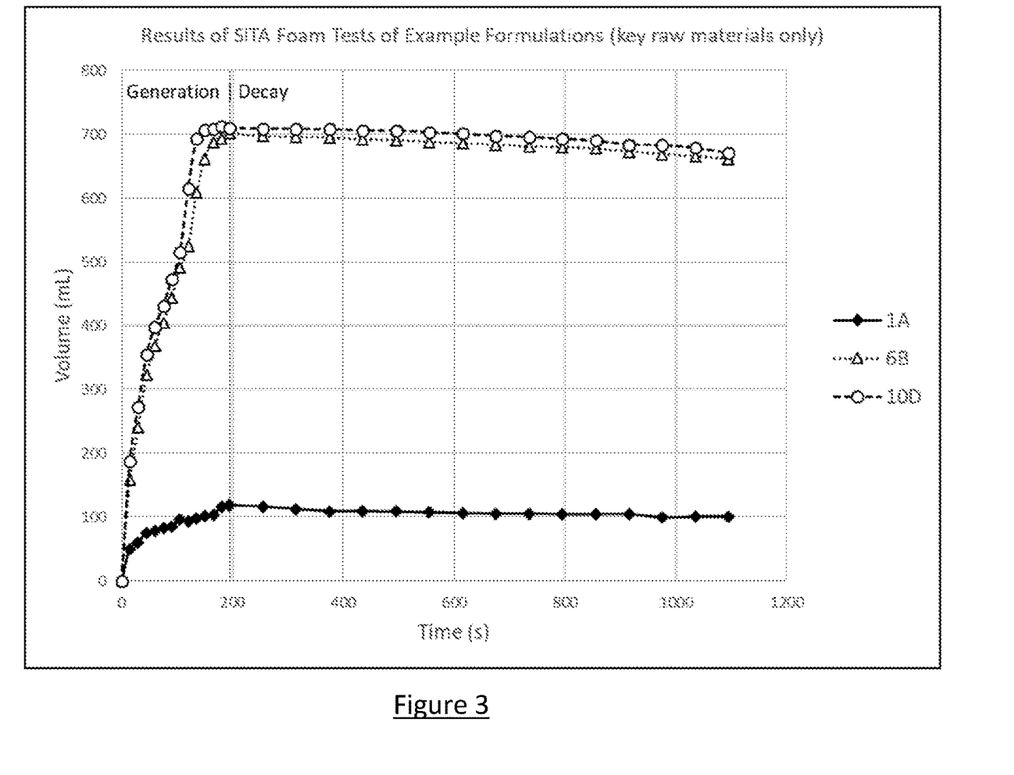
FIG. 3 is a graph depicting the results of foam tests of several Example formulations.

Example 1A passed the initial aesthetic evaluation and was subjected to the SITA Foam Test. Example 1A, however, was found to produce insufficient levels of foam (FIG. 3). Examples 2A-2D were found to not pass the initial aesthetic evaluation and were not subjected to further testing. Example 1A was tested for tablet-making, but it was found that there were manufacturing challenges in the powder sticking and poor flow of powdered materials.

A second product was made that was the same as Example 1A, except that the weight amount of sodium bicarbonate and citric acid were each increased to 10% each (by weight of the final product), and the weight amount of lactose monohydrate was reduced to 25% (by weight of the final product), and ProSolv SMCC HD 90 (JRS Pharma) was added in the amount of 10% (by weight of the final product) to improve binding. This new composition was tested for tablet making and showed sticking with poor flow of components. A third product was made that was the same as Example 1A, except that the weight amount of sodium cocoyl isethionate and sodium coco-sulfate were modified to each be 20% (by weight of the final product), the weight amount of lactose monohydrate was reduced to 24.75% (by weight of the final product), ProSolv SMCC HD 90 was added in the amount of 14% (by weight of the final product), and magnesium stearate was increased to a weight amount of 1.25% by weight of the final product). This new composition was tested for tablet making and the product showed sticking, with improved flow of the powdered materials.

Examples 3A-F

The next products were prepared to include 34% overall surfactants (in a 1:3 weight ratio) and included 30% buffering agents. The buffering agents were present in weight ratios of from 1:1 to 1:2. The formulations tested are in the Tables below:

| Component | Function | Example 3A | 3B | 3C | 3D | 3E | 3F |
|---|---|---|---|---|---|---|---|
| Sodium Cocoyl isethionate | First Surfactant | 8.5% | 8.5% | 8.5% | 8.5% | 8.5% | 8.5% |
| Sodium Coco-Sulfate | Second Surfactant | 25.5% | 25.5% | 25.5% | 25.5% | 25.5% | 25.5% |
| Zea May (Corn) Starch | Extender & Conditioning | 4.0% | 4.0% | 0.0% | 0.0% | 0.0% | 0.0% |
| Potassium Cetyl Phosphate | Emulsifying Agent | 0.0% | 0.0% | 4.0% | 4.0% | 2.0% | 2.0% |
| Sodium Bicarbonate | First Buffering Agent | 15.0% | 20.0% | 15.0% | 20.0% | 15.0% | 20.0% |
| Citric Acid | Second Buffering Agent | 15.0% | 10.0% | 15.0% | 10.0% | 15.0% | 10.0% |
| Lactose Monohydrate | Binding Agent | 31.0% | 31.0% | 31.0% | 31.0% | 33.0% | 33.0% |
| Magnesium Stearate | Lubricant | 1.0% | 1.0% | 1.0% | 1.0% | 1.0% | 1.0% |

Examples 3A-3F were prepared, but were found to not meet the initial aesthetic evaluation and therefore were not SITA Foam Tested nor attempted to be made into a tablet.

Examples 4A-4C

The next formulations were prepared to include 30% overall surfactants (in varying weight ratios of 1:1, 3:1, and 1:3) and included 36% buffering agents. The buffering agents were present in a weight ratio of 2:1. The formulations tested are in the Table below:

| Component | Function | Example 4A | Example 4B | Example 4C |
|---|---|---|---|---|
| Sodium Cocoyl isethionate | First Surfactant | 7.5% | 22.5% | 15.0% |
| Sodium Coco-Sulfate | Second Surfactant | 22.5% | 7.5% | 15.0% |
| Zea May (Corn) Starch | Extender & Conditioning | 0.0% | 0.0% | 0.0% |
| Potassium Cetyl Phosphate | Emulsifying Agent | 2.0% | 2.0% | 2.0% |
| Sodium Bicarbonate | Buffering Agent | 24.0% | 24.0% | 24.0% |
| Citric Acid | Buffering Agent | 12.0% | 12.0% | 12.0% |
| Lactose Monohydrate | Binding Agent | 31.0% | 31.0% | 31.0% |
| Magnesium Stearate | Lubricant | 1.0% | 1.0% | 1.0% |

Figure 2:
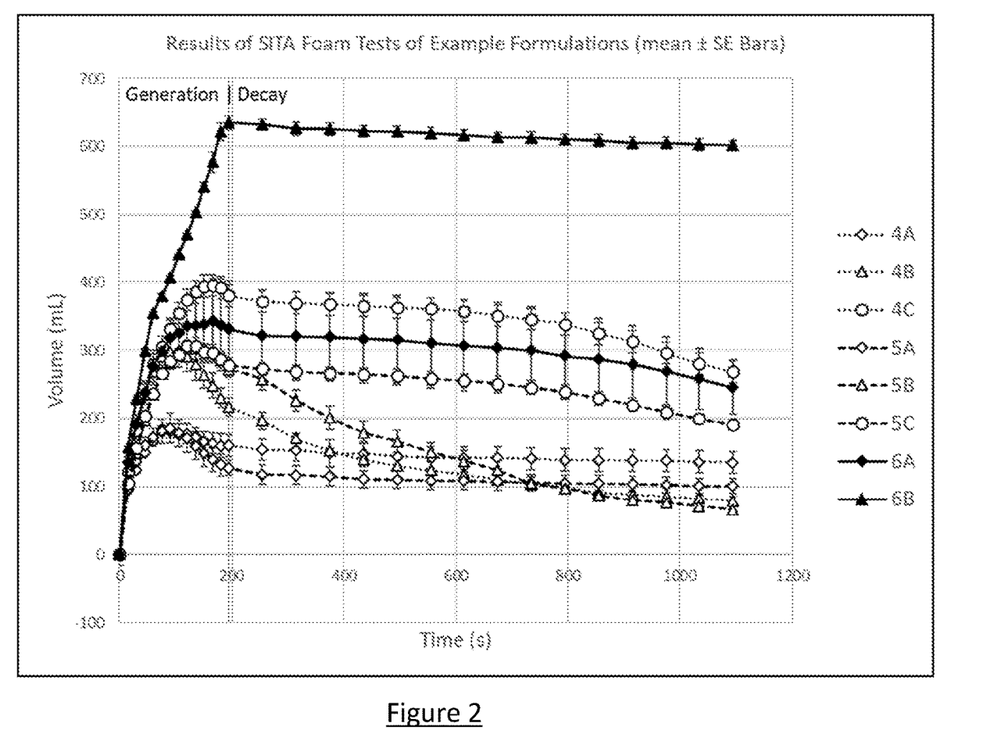
FIG. 2 is a graph depicting the results of foam tests of several Example formulations.

Examples 4A-4C were found to pass the initial evaluation and were subjected to the SITA Foam Test. Examples 4A-C were determined to have insufficient foaming profiles, as can be seen in FIG. 2.

Examples 5A-C

The next formulations were prepared to include 24% overall surfactants (in varying weight ratios of 1:1, 3:1, and 1:3) and included 42% buffering agents. The buffering agents were present in a weight ratio of 2:1. The formulations tested are in the Table below:

| Component | Function | Example 5A | Example 5B | Example 5C |
|---|---|---|---|---|
| Sodium Cocoyl isethionate | First Surfactant | 6.0% | 18.0% | 12.0% |
| Sodium Coco-Sulfate | Second Surfactant | 18.0% | 6.0% | 12.0% |
| Zea May (Corn) Starch | Extender & Conditioning | 0.0% | 0.0% | 0.0% |
| Potassium Cetyl Phosphate | Emulsifying Agent | 2.0% | 2.0% | 2.0% |
| Sodium Bicarbonate | Buffering Agent | 28.0% | 28.0% | 28.0% |
| Citric Acid | Buffering Agent | 14.0% | 14.0% | 14.0% |
| Lactose Monohydrate | Binding Agent | 31.0% | 31.0% | 31.0% |
| Magnesium Stearate | Lubricant | 1.0% | 1.0% | 1.0% |

Examples 5A-5C were found to pass the initial evaluation and were subjected to the SITA Foam Test. Examples 5A-5C were determined to have insufficient foaming profiles (see FIG. 2).

Example 6A and 6B

The next formulations were prepared to include 20% overall surfactants (in a weight ratio of 1:1) and included approximately 34% buffering agents. The buffering agents were present in a weight ratio of from 1:2 to 1:1. These formulations further included magnesium sulfate as an anticaking agent. The formulations tested are in the Table below:

| Component | Function | Example 6A | Example 6B |
|---|---|---|---|
| Sodium Cocoyl isethionate | First Surfactant | 10.0% | 10.0% |
| Sodium Coco-Sulfate | Second Surfactant | 10.0% | 10.0% |
| Potassium Cetyl Phosphate | Emulsifying Agent | 2.0% | 2.0% |
| Sodium Bicarbonate | First Buffering Agent | 23.0% | 17.0% |
| Citric Acid | Second Buffering Agent | 11.5% | 17.0% |
| Magnesium Sulfate | Anticaking | 11.5% | 12.0% |
| Lactose Monohydrate | Binding Agent | 30.5% | 30.5% |

-continued

| Component | Function | Example 6A | Example 6B |
|---|---|---|---|
| Silica | Anticaking Agent | 0.5% | 0.5% |
| Magnesium Stearate | Lubricant | 1.0% | 1.0% |

Example 6A was found to pass the initial evaluation and was subjected to the SITA Foam Test. Example 6A was determined to have an insufficient foaming profile.

Example 6B passed the initial evaluation and was subjected to the SITA Foam Test. Example 6B appeared to have a quick and pronounced volume of foam generated with a desirable foam stability. As shown in FIG. 2, Example 6B generated a Peak Foam Volume greater than 600 mL and Foam Decay was only 4% in 10 minutes. Further, formulation of Example 6B provided a pleasant skin feel and improved aesthetics. The foaming profile and pleasant skin feel results for Example 6B were found to be acceptable.

Examples 7A and 7B

The next formulations were prepared to include 18% overall surfactants (in a weight ratio of 1:1) and included 36% buffering agents. The buffering agents were present in weight ratios of from 1:2 to 1:1. These formulations further included magnesium sulfate as an anti-caking agent. The formulations formed are set forth in the Table below:

| Component | Function | Example 7A | Example 7B |
|---|---|---|---|
| Sodium Cocoyl isethionate | First Surfactant | 9.0% | 9.0% |
| Sodium Coco-Sulfate | Second Surfactant | 9.0% | 9.0% |
| Potassium Cetyl Phosphate | Emulsifying Agent | 2.0% | 2.0% |
| Sodium Bicarbonate | First Buffering Agent | 24.0% | 18.0% |
| Citric Acid | Second Buffering Agent | 12.0% | 18.0% |
| Magnesium Sulfate | Anticaking | 12.0% | 12.0% |
| Lactose Monohydrate | Binding Agent | 30.5% | 30.5% |
| Silica | Anticaking Agent | 0.5% | 0.5% |
| Magnesium Stearate | Lubricant | 1.0% | 1.0% |

Examples 7A-7B were found to pass the aesthetic evaluation, but appeared to have less aesthetic foam generation than Example 6B, and were not submitted to the SITA Foam Test.

Examples 8A and 8B

The next formulations were prepared to include 15% overall surfactants (in a weight ratio of 1:1) and included 39% buffering agents. The buffering agents were present in weight ratios of from 1:2 to 1:1. These formulations further included magnesium sulfate as an anti-caking agent. The formulations as prepared are set forth in the Table below:

| Component | Function | Example 8A | Example 8B |
|---|---|---|---|
| Sodium Cocoyl isethionate | First Surfactant | 7.5% | 7.5% |
| Sodium Coco-Sulfate | Second Surfactant | 7.5% | 7.5% |
| Potassium Cetyl Phosphate | Emulsifying Agent | 2.0% | 2.0% |
| Sodium Bicarbonate | First Buffering Agent | 26.0% | 19.0% |
| Citric Acid | Second Buffering Agent | 13.0% | 19.0% |
| Magnesium Sulfate | Anticaking Agent | 12.0% | 13.0% |
| Lactose Monohydrate | Binding Agent | 30.5% | 30.5% |
| Silica | Anticaking Agent | 0.5% | 0.5% |
| Magnesium Stearate | Lubricant | 1.0% | 1.0% |

Examples 8A-8B were found to pass the aesthetic evaluation, but appeared to have less aesthetic foam generation than Example 6B, and were not submitted to the SITA Foam Test.

Examples 9a to 9F

Based upon the earlier studies, it was determined that the surfactant amount of approximately 18-20%, with buffering agents amount higher than the amount of surfactant, plus the presence of magnesium sulfate, had demonstrated surprisingly effective results. Also, surfactant ratios and buffering agent ratios were major factors. The next formulations included varying levels of these components, with the surfactant amount remaining at 18% by weight. The formulations prepared are set forth in the Table below:

| Component | Function | Example 9A | 9B | 9C | 9D | 9E | 9F |
|---|---|---|---|---|---|---|---|
| Sodium Cocoyl isethionate | First Surfactant | 9.0% | 9.0% | 13.5% | 13.5% | 4.5% | 4.5% |
| Sodium Coco-Sulfate | Second Surfactant | 9.0% | 9.0% | 4.5% | 4.5% | 13.5% | 13.5% |
| Potassium Cetyl Phosphate | Emulsifying Agent | 2.0% | 2.0% | 2.0% | 2.0% | 2.0% | 2.0% |
| Sodium Bicarbonate | First Buffering Agent | 28.0% | 30.0% | 28.0% | 30.0% | 28.0% | 30.0% |
| Citric Acid | Second Buffering Agent | 14.0% | 15.0% | 14.0% | 15.0% | 14.0% | 15.0% |
| Magnesium Sulfate | Anticaking agent | 6.0% | 3.0% | 6.0% | 3.0% | 6.0% | 3.0% |
| Lactose Monohydrate | Binding Agent | 30.5% | 30.5% | 30.5% | 30.5% | 30.5% | 30.5% |
| Silica | Anticaking agent | 0.5% | 0.5% | 0.5% | 0.5% | 0.5% | 0.5% |
| Magnesium Stearate | Lubricant | 1.0% | 1.0% | 1.0% | 1.0% | 1.0% | 1.0% |

Examples 9A-9F were each prepared but found to not pass the aesthetic evaluation and therefore were not subjected to the SITA Foam Test.

Examples 10a to 10D

To compare various products with varying levels of magnesium sulfate, the next formulations were prepared to include 18% surfactant in a 1:1 ratio, and varying levels of buffering agents and magnesium sulfate. The formulations prepared are set forth in the Table below:

| Component | Function | Example 10A | Example 10B | Example 10C | Example 10D |
|---|---|---|---|---|---|
| Sodium Cocoyl isethionate | First Surfactant | 9.0% | 9.0% | 9.0% | 9.0% |
| Sodium Coco-Sulfate | Second Surfactant | 9.0% | 9.0% | 9.0% | 9.0% |
| Potassium Cetyl Phosphate | Emulsifying Agent | 2.0% | 2.0% | 2.0% | 2.0% |
| Sodium Bicarbonate | First Buffering Agent | 24.0% | 22.5% | 21.0% | 19.5% |
| Citric Acid | Second Buffering Agent | 24.0% | 22.5% | 21.0% | 19.5% |
| Magnesium Sulfate | Anticaking Agent | 0.0% | 3.0% | 6.0% | 9.0% |
| Lactose Monohydrate | Binding Agent | 30.5% | 30.5% | 30.5% | 30.5% |
| Silica | Anticaking Agent | 0.5% | 0.5% | 0.5% | 0.5% |
| Magnesium Stearate | Lubricant | 1.0% | 1.0% | 1.0% | 1.0% |

Figure 4:
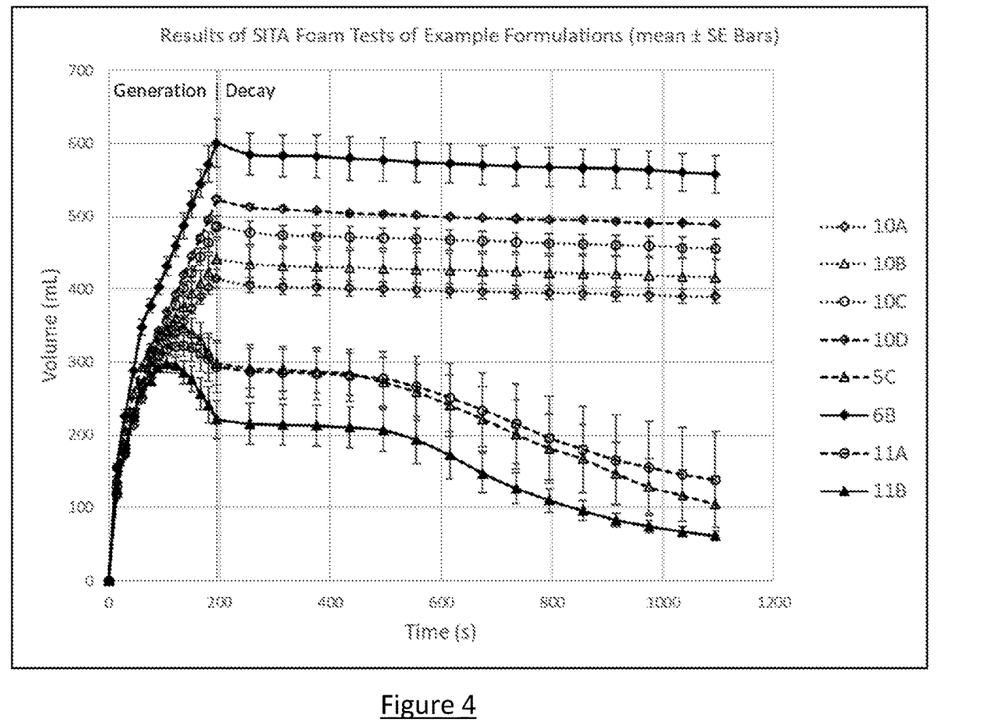
FIG. 4 is a graph depicting the results of foam tests of several Example formulations.

Examples 10A-10D were prepared, all passed the aesthetics evaluation, and all were subjected to the SITA Foam Test (results of which are shown in FIG. 4). These results show a dose response in Peak Foam Volume with magnesium sulfate level. Example 10D (with 9% magnesium sulfate) had the highest Peak Foam Volume which exceeds 500 mL. All 10A-10D Examples showed Foam Decay less than 6% after 10 minutes.

A second formula was made that tracks Example 10D, except the lactose monohydrate was reduced to 21% by weight of the final product, ProSolv SMC HD90 was added in an amount of 10% by weight of the final product, and the silica was removed. This second formula was used to try to make a tablet, but the tablet friability was insufficient and there was tablet edge erosion.

A third formula was made that tracks Example 10D, except the lactose monohydrate was removed, ProSolv SMC HD 90 was added in an amount of 31% by weight of the final product, and silica was removed. This third formula was used to try to make a tablet, and there was found to be less sticking of components during manufacture, however, the tablet formed was eroded and did not pass.

A fourth formula was made that tracks Example 10D, except the lactose monohydrate was removed, ProSolv SMC HD 50 (JRS Pharma) was added in an amount of 31% by weight of the final product, and silica was removed. This fourth formula was used to try to make a tablet and it was found that there was little to no sticking of components, there was acceptable component flow during manufacture, and the resulting table had the appropriate friability and softness to allow a user to crush the tablet during use. This fourth variation of Example 10D was found to be acceptable as a formed tablet.

As described above, through the experiments set forth above, it was determined that a suitable foaming composition can be prepared using a relatively lower amount of surfactants (about 18% by weight) compared to the buffering agents (about 36-40% by weight), coupled with the presence of magnesium sulfate. It was unexpected that the presence of magnesium sulfate would have resulted in a noticeable difference in foaming profile, including Peak Foam Volume and foam stability. It was determined that the ratios of first and second surfactants, as well as the total weight of the surfactants, and the ratio of the first and second buffering agents may have an impact on the performance of the final product. In addition, the total combined amount of the surfactant and buffering agents may have an effect when the total amount is from about 50% to about 80% by weight of the final product. For example, see the below Table summarizing the total amounts:

| Formula | Total Surfactants % | Total Buffering Agents % | Anticaking agent % | Total % |
|---|---|---|---|---|
| Example 1A | 40 | 16 | 0 | 56 |
| Example 6B | 20 | 34 | 12 | 66 |
| Example 10D | 18 | 39 | 9 | 66 |

FIG. 2 shows a graph demonstrating the results of an enhanced foaming profile for example 6B with a Peak Foam Volume of 635 ml and Foam Decay of 4% in 10 minutes. As can be seen, Example 6B shows a quick and voluminous foaming profile very rapidly, as well as a slow foam decay.

Similarly, FIG. 3 shows the results of the key raw materials (surfactants, buffering agents, and magnesium sulfate only) sampled in Example 1A, Example 6B and Example 10D. As can be seen, 6B and 10D were very similar in Peak Foam Volume and foam stability (i.e., Peak Foam Volumes greater than 700 ml and Foam Decay of less than 4% in 10 minutes). Each of these formulations performed considerably better than Example 1A which had a Peak Foam Volume of only 118 mL and Foam Decay of 12% in 10 minutes. Therefore, Examples 6B and 10D were deemed effective.

Examples 11-12

As a result of the above experiments, and to confirm the aforementioned results, various Examples were prepared again, and new formulations were prepared. The formulations of Examples 5C, 6B, 10A, 10B, 10C, and 10D were prepared using the same formulation described above. New formulations 11A and 11B were prepared, which included higher levels of one of the buffering agents, and also included varying ratios of the buffering agents (e.g., not 1:1 ratio). New formulations 12A-C were also prepared, as shown in the Tables below:

|  |  | Example | | | | |
|---|---|---|---|---|---|---|
| Component | Function | 11A | 11B | 12A | 12B | 12C |
| Sodium Cocoyl isethionate | First Surfactant | 9.0% | 9.0% | 9.0% | 15.0% | 9.0% |
| Sodium Coco-Sulfate | Second Surfactant | 9.0% | 9.0% | 9.0% | 15.0% | 9.0% |
| Potassium Cetyl Phosphate | Emulsifying Agent | 2.0% | 2.0% | 2.0% | 2.0% | 2.0% |
| Sodium Bicarbonate | First Buffering Agent | 23.7% | 26.3% | 24.0% | 24.0% | 24.0% |
| Citric Acid | Second Buffering Agent | 18.3% | 20.3% | 24.0% | 24.0% | 24.0% |
| Magnesium Sulfate | Anticaking Agent | 6.0% | 6.0% | 9.0% | 0.0% | 0.0% |
| Lactose Monohydrate | Binding Agent | 30.5% | 25.9% | 21.5% | 18.5% | 21.5% |
| Silica | Anticaking Agent | 0.5% | 0.5% | 0.5% | 0.5% | 0.5% |
| Magnesium Stearate | Lubricant | 1.0% | 1.0% | 1.0% | 1.0% | 1.0% |
| Sodium Chloride | Viscosity Increasing Agent | 0.0% | 0.0% | 0.0% | 0.0% | 9.0% |

Each formulation was subjected to the SITA Foam Test. As was consistent with the Example above, Example 6B produced the most favorable results, with a Peak Foam Volume of 600 mL and Foam Decay of less than 6% in 10 minutes. Examples 10A-10D also showed favorable results, with Example 10D having the best results, followed by, in order, Examples 10C, 10B, and 10A. This shows a dose response to magnesium sulfate level. Examples 5C, 11A and 11B performed poorly, despite overlap in ingredients. The results demonstrate that unequal levels of buffering agents and/or high levels of one of the buffering agents appears to be detrimental to the Peak Foam Volume and/or the foam stability. FIG. 4 shows the results of these tests.

Figure 5:
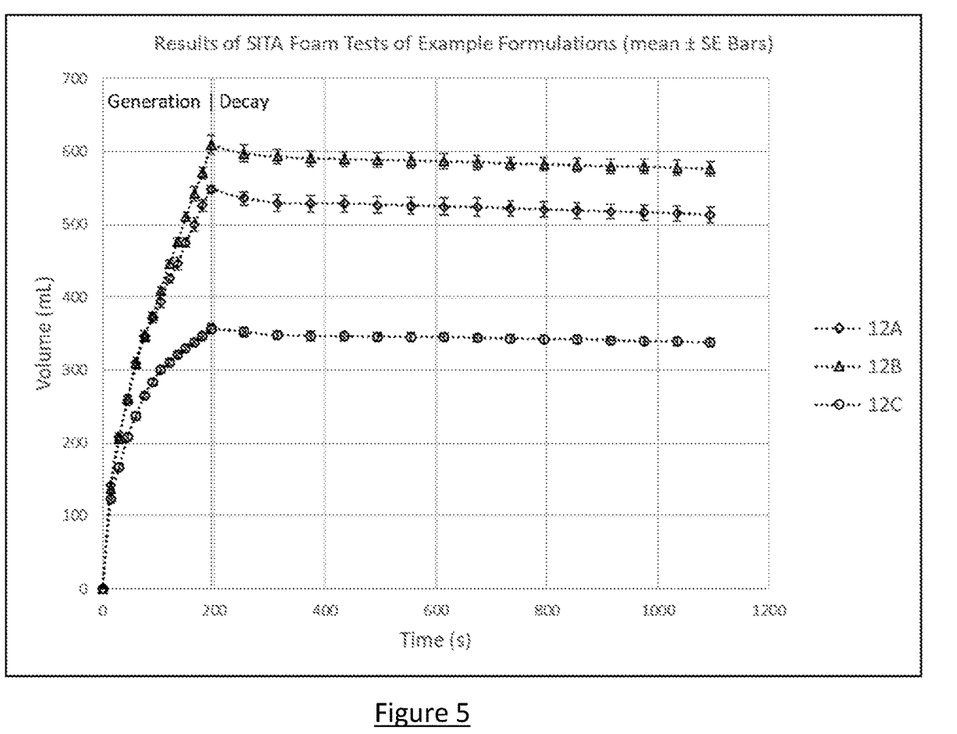
FIG. 5 is a graph depicting the results of foam tests of several Example formulations.

FIG. 5 shows the results of Examples 12A-12C. The results show additional evidence of the effect of magnesium sulfate on the foaming profile. Example 12C showed the lowest Peak Foam Volume of only 357 mL. Example 12B showed the highest Peak Foam Volume at 610 mL, and Example 12A showed a Peak Foam Volume of 548 mL.

This shows that for compositions including the two surfactants at 15% weight each (i.e., 12B), there is a significant volume of foam generated. In Example 12C the magnesium sulfate was replaced with another salt, sodium chloride, commonly used in cleanser. However, when compared to a composition including the surfactants at 9% each and no magnesium sulfate (i.e., 12C), the Foam Volume was much lower. When the two surfactants at 9% each were also combined with magnesium sulfate (i.e., 12A), the Foam Volume was nearly as high as that generated by high surfactant levels without magnesium sulfate. This provides a significant benefit of having the ability to reduce surfactant levels in the inventive formulations, replacing with magnesium sulfate, which provides a number of benefits to the user, including cost.

Example 13

Based upon the results generated above, the foam generated by individual surfactants (sodium cocoyl isethionate and sodium coco-sulfate) was tested using the SITA Foam Test. Formulation S1 included sodium cocoyl isethionate by itself and Formulation S2 included sodium coco-sulfate by itself. Since these were single ingredient formulations, the SITA Foam Test sample sizes were adjusted so that the surfactant levels were equivalent to 9% had they been complete formulations which would be tested at 0.25 gm per 250 gm of hard water. Formulations S1 and S2 were tested at 0.0225 gm per 250 gm of hard water (i.e., 9% of 0.25 gm).

Figure 6:
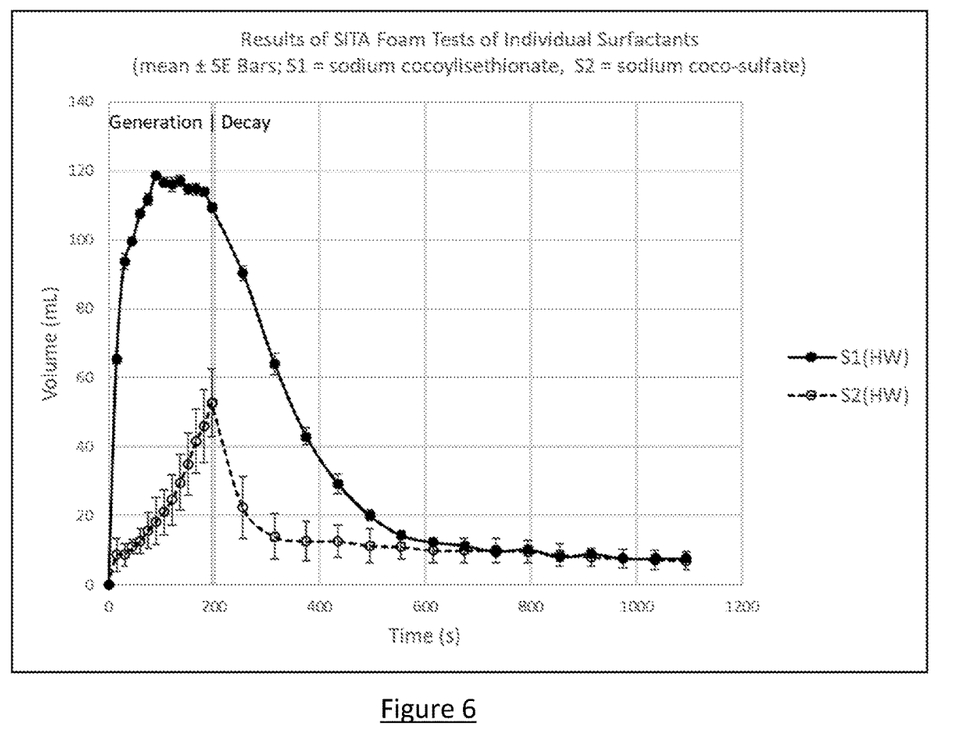
FIG. 6 is a graph depicting the results of foam tests of individual surfactants.

As can be seen in FIG. 6, the volume of foam generated by the surfactants themselves was significantly lower than the mixture of the surfactant and other ingredients. In addition, the foam stability was also significantly weaker than the mixture of the surfactants plus other components. This demonstrates that the full compositions described above perform more effectively than the use of surfactants themselves.

To determine the impact of the combined surfactants plus magnesium sulfate and no other ingredients, two compositions were also prepared for comparison. Examples 13A and 13B below each contain two surfactants and magnesium sulfate in 3:3:1 and 1:1:1 weight ratios respectively. Since these were partial formulations, the SITA Foam Test sample sizes were adjusted so that the surfactant levels were equivalent to 9% had they been complete formulations (for example, as in Example 10B and Example 10D, which were tested at 0.25 gm per 250 gm of hard water). Example 13A was tested at 0.0525 gm per 250 gm of hard water and Example 13B was tested at 0.0675 gm per 250 gm of hard water.

| Component (g) | Function | Example 13A (ratio by weight) | Example 13B (ratio by weight) |
|---|---|---|---|
| Sodium Cocoyl isethionate | First Surfactant | 3 | 1 |
| Sodium Coco-Sulfate | Second Surfactant | 3 | 1 |
| Magnesium Sulfate | Anti-Caking | 1 | 1 |

Figure 7:
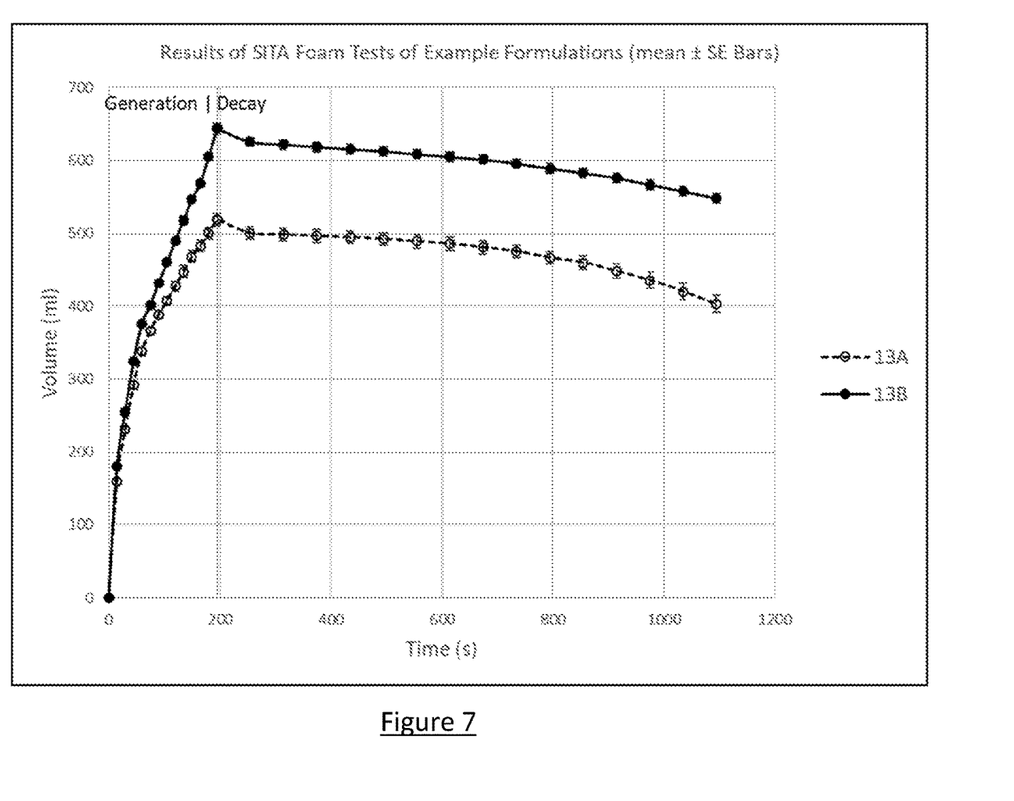
FIG. 7 is a graph depicting the results of foam tests of Example formulation with varying levels of magnesium sulfate.

Each of Examples 13A and 13B were tested using the SITA Foam Test. Results are shown in FIG. 7. As can be seen, the combination of just the two surfactants plus magnesium sulfate provided higher Peak Foam Volumes and suitable foam stability, even without the presence of the buffering agents. Thus, the presence of magnesium sulfate, even without other agents that would be likely to provide additional foam, increased the Foam Volume. It is notable, however, that the foam stability of the Examples 13A and 13B was less desirable than in the Examples in which the full formulation was tested (e.g., Examples 6B and 10D).

Based upon this test, it can be concluded that the presence of magnesium sulfate is helpful in adding to the volume of foam generated, however, the lower the level of magnesium sulfate, the quicker the Foam Decays. In addition, even with the magnesium sulfate at the same level as each of the surfactants (Example 13B), the foam began to decay faster than the full formulations noted above (Examples 10B and 10D).

The invention claimed is:

1. A method of cleansing the skin of a user, comprising the steps of:
 a. removing a solid cleansing product from a container, the solid cleansing product comprising:
  (i) at least a first surfactant and at least a second surfactant, wherein the second surfactant comprises a sulfate, the first surfactant and second surfactant are present in a combined surfactant weight amount, and wherein the first surfactant and the second surfactant are present in a weight ratio of from 1:1 to about 1:1.5;
  (ii) at least a first buffering agent and at least a second buffering agent, wherein the first buffering agent and second buffering agent are present in a combined buffering agent weight amount; and
  (iii) magnesium sulfate;
  wherein the combined buffering agent weight amount is greater than the combined surfactant weight amount,
  wherein the solid cleansing product is suitable for use on a user's skin, hair or face,
  wherein the first buffering agent is a basic buffering agent, and
  wherein the second buffering agent is an acidic buffering agent;
 b. combining the solid cleansing product with water; and
 c. subjecting the combined solid cleansing product and water to agitation against the user's skin for at least 10 seconds;
 whereby the agitation causes the combined solid cleansing product and water to form a foamed cleansing product.

2. The method of claim 1, wherein the combined buffering agent weight amount is at least two times the combined surfactant weight amount.

3. The method of claim 1, wherein the combined buffering agent weight amount is approximately two times the combined surfactant weight amount.

4. The method of claim 1, wherein the combined surfactant weight amount is about 16% to about 20% by weight of the solid cleansing product.

5. The method of claim 1, wherein the combined surfactant weight amount is about 18% by weight of the solid cleansing product.

6. The method of claim 1, wherein the combined buffering agent weight amount is about 36% to about 48% by weight of the solid cleansing product.

7. The method of claim 1, wherein the combined buffering agent weight amount is about 36% by weight of the solid cleansing product.

8. The method of claim 1, wherein the combined surfactant weight amount is about 1.5 to about 3 times the weight amount of magnesium sulfate in the solid cleansing product.

9. The method of claim 1, wherein the magnesium sulfate weight amount is about 6% to about 12% by weight of the solid cleansing product.

10. The method of claim 1, wherein the first surfactant is an isethionate.

11. The method of claim 1, wherein the cleansing product has a peak foam volume of greater than 500 mL, as measured by mixing 0.25 g of cleansing product and 250 mL of water in a SITA Foam Tester.

12. The method of claim 1, wherein the cleansing product has a foam decay level of less than 10% after 10 minutes from reaching its peak foam volume.

13. The method of claim 1, wherein the solid cleansing product is in the form of a loose powder.

14. The method of claim 1, wherein the solid cleansing product is in the form of a pressed tablet.

15. The method of claim 14, wherein the pressed tablet further includes a binding agent.

16. The method of claim 1, wherein the first and second surfactants are each independently sulfate-containing surfactants.

* * * * *